US010561505B2

(12) United States Patent
Brehm

(10) Patent No.: US 10,561,505 B2
(45) Date of Patent: Feb. 18, 2020

(54) DEVICE FOR ATTACHING A POSITIONING DEVICE TO A BONE OF A PATIENT, DEVICE FOR TREATING A BONE OF A PATIENT, AND HIP IMPLANT SYSTEM

(71) Applicant: Peter Brehm, Weisendorf (DE)

(72) Inventor: Peter Brehm, Weisendorf (DE)

( * ) Notice: Subject to any disclaimer, the term of this patent is extended or adjusted under 35 U.S.C. 154(b) by 505 days.

(21) Appl. No.: 15/306,188

(22) PCT Filed: Apr. 24, 2015

(86) PCT No.: PCT/EP2015/058933
§ 371 (c)(1),
(2) Date: Oct. 24, 2016

(87) PCT Pub. No.: WO2015/165817
PCT Pub. Date: Nov. 5, 2015

(65) Prior Publication Data
US 2017/0042702 A1 Feb. 16, 2017

(30) Foreign Application Priority Data

May 2, 2014 (DE) .................. 10 2014 208 283

(51) Int. Cl.
*A61F 2/46* (2006.01)
*A61B 17/17* (2006.01)
(Continued)

(52) U.S. Cl.
CPC ........ *A61F 2/4684* (2013.01); *A61B 17/1746* (2013.01); *A61B 90/06* (2016.02); *A61B 2090/062* (2016.02); *A61F 2/32* (2013.01)

(58) Field of Classification Search
CPC .. A61F 2/4684; A61F 2/4609; A61B 17/1746; A61B 17/1666
See application file for complete search history.

(56) References Cited

U.S. PATENT DOCUMENTS 6,416,553 B1 * 7/2002 White ............... A61B 17/1666
623/22.38
2005/0107799 A1 5/2005 Graf et al. .................... 606/91
(Continued)

FOREIGN PATENT DOCUMENTS

| JP | H0444758 | 2/1992 |
| JP | 2013537454 | 10/2013 |
| WO | WO 2007/118708 | 10/2007 |

OTHER PUBLICATIONS

Report or action dated Jan. 13, 2015 in corresponding German Application No. 10 2014 208 283.8.
(Continued)

*Primary Examiner* — Matthew J Lawson
(74) *Attorney, Agent, or Firm* — Fattibene and Fattibene LLC; Paul A. Fattibene

(57) ABSTRACT

A device for attaching a positioning device to a bone of a patient at a predetermined position relative to a hip implant comprising a trial hip implant and a template. The trial hip implant has a support surface for resting on the bone of the patient The template can be secured to the trial hip implant and has at least one cylindrical opening with a longitudinal axis. The trial hip implant is shaped such that any straight line which runs through one of the at least one cylindrical opening and is parallel to the longitudinal axis of the respective opening does not intersect the trial hip implant when the template is secured to the trial hip implant.

16 Claims, 15 Drawing Sheets

(51) Int. Cl.
*A61B 90/00* (2016.01)
*A61F 2/32* (2006.01)

(56) References Cited

U.S. PATENT DOCUMENTS

| | | | |
|---|---|---|---|
| 2006/0116680 A1* | 6/2006 | Kugler | A61B 17/92 |
| | | | 606/86 B |
| 2006/0161167 A1 | 7/2006 | Myers et al. | 606/91 |
| 2008/0009874 A1 | 1/2008 | Meridew et al. | 606/81 |
| 2011/0087230 A1 | 4/2011 | Graf et al. | 606/87 |
| 2012/0109137 A1* | 5/2012 | Iannotti | A61B 17/1728 |
| | | | 606/87 |
| 2012/0245702 A1* | 9/2012 | Pappas | A61F 2/30734 |
| | | | 623/22.12 |
| 2012/0289965 A1* | 11/2012 | Gelaude | A61B 17/15 |
| | | | 606/87 |
| 2013/0245631 A1 | 9/2013 | Bettenga | 606/91 |
| 2014/0107651 A1 | 4/2014 | Meridew et al. | 606/80 |
| 2014/0163564 A1* | 6/2014 | Bollinger | A61B 17/1666 |
| | | | 606/91 |
| 2014/0276870 A1* | 9/2014 | Eash | A61B 17/1746 |
| | | | 606/91 |
| 2014/0364858 A1* | 12/2014 | Li | A61F 2/4609 |
| | | | 606/91 |
| 2015/0012001 A1* | 1/2015 | Theiss | A61B 17/175 |
| | | | 606/87 |
| 2015/0112348 A1* | 4/2015 | Schoenefeld | A61B 17/1746 |
| | | | 606/87 |

OTHER PUBLICATIONS

Notice of Reasons for Rejection in corresponding Japanese Application No. 2016-563952 dated Sep. 5, 2017, with English translation, 13 pages.
Notice of Rejection in corresponding Japanese Application No. 2016-563952 believed dated Jul. 5, 2018, with English translation, 7 pages.

* cited by examiner

DEVICE FOR ATTACHING A POSITIONING DEVICE TO A BONE OF A PATIENT, DEVICE FOR TREATING A BONE OF A PATIENT, AND HIP IMPLANT SYSTEM

FIELD OF THE INVENTION

The invention relates generally to hip implants, in particular to hip implant systems with augments that can be secured to a hip implant and devices that can be used to treat a bone of a patient during the implantation of such hip implants.

BACKGROUND OF THE INVENTION

Artificial hip joints can comprise a femoral component with a shaft to be inserted into the femur of the patient and an artificial joint ball, as well as an artificial joint socket which is attached to the hip bone of the patient.

In some cases, for example, when the hip prosthesis of a patient has become loose, it may be necessary to perform revision surgery in which the hip joint prosthesis is completely or partially replaced. During partial replacement of the hip joint prosthesis, either the artificial joint socket or the femoral component of the hip joint prosthesis can be replaced.

In particular in revision surgery in which the entire artificial hip joint is replaced, or in surgery where the artificial joint socket is replaced, difficulties can arise due to bone defects in the hip bone of the patient. In view of this situation, special hip implants have been designed for securing an artificial joint socket to the hip bone of a patient in revision surgery.

A modular hip implant according to prior art that can be used in revision surgery, in which the acetabulum of the patient is replaced, is described in WO 2007/118708 A2. The modular hip implant comprises a base that is to be attached to a hipbone and a socket for accommodating a hip joint prosthesis. The base is provided with fastening means for mounting the base on the hipbone as well as a concave receiving area for the socket. The socket has a convex outer form which is complementary to the receiving area such that the radii of curvature determining the concave receiving area and the convex outer form essentially correspond to each other. The socket can be fastened within the base. The base and/or the socket encompass means for adjusting the position of the socket relative to the base. This allows the inclination and the anteversion to be adjusted by suitably arranging the socket in the base. To enable reliably securing the base to the hipbone also in the case of bone defects, cranial plates can be provided having holes into which bone screws can be inserted for screwing the base to the bone of the patient, and a caudal attachment hook can be provided on the base.

While it may be sufficient in some cases to attach the base of the hip implant to the hip bone of the patient and to perform reconstruction of the bone defects of the patient with the help of natural bone material, which can be introduced, for example, through an opening in the base of the hip implant, it can in other cases be advisable to use a so-called augment to fill gaps between the base of the hip implant and the bone of the patient which are caused by bone defects. Such an augment can be formed from metal having a porous structure in order to enhance adherence of the augment to the bone of the patient and it can be attached with the aid of screws and/or bone cement to the hip implant.

It can when using augments be necessary to treat the bone of the patient in order to adapt the shape of the gap between the hip implant and the bone of the patient for accommodating the augment in the gap.

Bone milling devices which are operated by a doctor in an unsupported manner can be used for this purpose. Unsupported milling, however, is tedious and relatively inaccurate, so that there is a risk that too much bone material of the patient is removed.

SUMMARY OF THE INVENTION

It is an object of the invention to provide devices and systems with which the above described drawbacks of prior art can be completely or partially avoided.

According to the invention, the object is achieved by a device for attaching a positioning device to a bone of a patient at a predetermined position relative to a hip implant. The device comprises a trial hip implant and a template. The trial hip implant has a support surface for resting on the bone of the patient. The template can be secured to the trial hip implant and has at least one cylindrical opening with a longitudinal axis. The trial hip implant is shaped such that any straight line which runs through a cylindrical opening and is parallel to the longitudinal axis of the respective opening does not intersect the trial hip implant when the template is secured to the trial hip implant.

A positioning device, for example, a bone screw can be attached to the bone of the patient through the at least one cylindrical opening of the template, where the position of the positioning device relative to the trial hip implant is defined in at least two axes that are perpendicular to the longitudinal axis of the cylindrical opening of the template. The positioning device can after removal of the trial hip implant and the template from the bone be used for guiding a machining tool, such as for example a bone milling device. The bone of the patient can thereby be treated selectively and with relatively high accuracy at locations that are located in specific positions relative to the trial hip implant. Since the support surface of the trial hip implant can have a shape that substantially corresponds to the shape of the support surface of the final hip implant, the trial hip implant can be located relative to the bone of the patient in substantially the same position as the final hip implant. The bone of the patient can thereby be treated in the surrounding of the final hip implant with relatively high accuracy, in particular at a location where an augment is attached to the hip implant.

In some embodiments, the template comprises several cylindrical openings that are arranged in a row. This positioning device can therewith by use of the same template be positioned relative to the trial hip implant at several different positions. The differently sized regions of the bone of the patient can thereby be treated as needed, in particular depending on the size of an augment used.

In some embodiments, the longitudinal axes of the cylindrical openings of the template are substantially parallel to each other.

In some embodiments, the template on a side facing away from the trial hip implant when the template is secured to the trial hip implant has a stepped surface with several steps, where one of the several cylindrical openings extends through each of the steps. The steps can serve as a reference for positioning a positioning device which is attached through one of the cylindrical openings to the bone of the patient in a direction parallel to the longitudinal axis of the cylindrical opening. The position of the positioning device relative to the trial hip implant can thereby be adjusted accurately also in an axis which is parallel to the longitudinal axis of the cylindrical opening.

In some embodiments, at least a portion of each of the steps has a surface which is perpendicular to the longitudinal axis of the cylindrical opening extending through the respective step. Particularly precise positioning of a positioning device, which is attached through one of the cylindrical openings to the bone of the patient, is thereby enabled along the axis that is parallel to the longitudinal direction of the cylindrical opening.

In some embodiments, the trial hip implant comprises a section having a general shape of a spherical dome shell and an edge section, and the template on a side facing the trial hip implant when the template is secured to the trial hip implant has a surface with a section having a shape that is complementary to the edge section. This can achieve particularly stable support of the template on the trial hip implant.

The trial hip implant in some embodiments has a slit-shaped notch that extends through the section having the general shape of a spherical dome shell and the edge section, wherein it is true for at least one cylindrical opening that any straight line, extending through the opening and being parallel to the longitudinal axis of the opening, extends through the slit-shaped notch when the template is secured to the trial hip implant. It can in a particularly simple manner be ensured by the slit-shaped notch, being provided on the trial hip implant but not needing to be present on the final hip implant, that no parts of the trial hip implant are present between the bone of the patient and the template, which would interfere when attaching a positioning device through a cylindrical opening of the template.

In some embodiments, the trial hip implant on a first side of the slit-shaped notch comprises an opening in the edge section. The template comprises a protrusion that is complementary to the opening in the edge section and engages in the opening in the edge section when the template is secured to the trial hip implant. On a second side of the slit-shaped notch, the trial hip implant comprises a threaded opening in the edge section having an internal thread. The template comprises an opening that is separate from said at least one cylindrical opening and is flush with the threaded opening in the edge section when the template is secured to the trial hip implant. The device additionally comprises a screw with an external thread that is complementary to the internal thread in the threaded opening in the edge section for screwing the template to the trial hip implant.

With the threaded opening in the edge section, with the opening in the template being flush with the threaded opening in the edge section, and the screw, the template can be fixed to the trial hip implant in a stable manner. Rotation of the template about the longitudinal axis of the screw relative to the trial hip implant can be prevented due to the opening in the edge section of the trial hip implant on the side of the slit-shaped notch opposite to the threaded opening and the protrusion of the template complementary to this opening.

In some embodiments, the device additionally comprises a drill guide which is insertable through the at least one cylindrical opening of the template and comprises a channel through which a bone drill is guidable. With the aid of the drill bit guided through the channel of the drill guide, the bone of the patient can be pre-drilled prior to attaching the positioning device. It can with the drill guide be ensured that the drill bit is aligned parallel to the longitudinal axis of the cylindrical opening, although the diameter of the drill is smaller than the diameter of the cylindrical opening.

In some embodiments, the device additionally comprises a positioning device. The positioning device comprises a cylindrical guide section with a longitudinal axis which can be guided through the at least one cylindrical opening of the template. The guide section is thereby movable relative to the template along the longitudinal axis of the cylindrical opening, and the longitudinal axis of the guide section is aligned along the longitudinal axis of the cylindrical opening. By using a positioning device thus formed, particularly accurate positioning of the positioning device in the bone of the patient can be achieved.

In some embodiments, the device additionally comprises a tool for securing the positioning device to the bone of the patient through a cylindrical opening of the template. The tool comprises a stop for defining a distance between a distal end of the positioning device secured to the bone of the patient and the end of the cylindrical opening of the template that faces away from the sample implant and through which the positioning device is secured to the bone of the patient. The positioning device can therewith be positioned in a particularly simple manner along the axis that is parallel to the longitudinal axis of the cylindrical opening.

In some embodiments, the positioning device comprises a bone screw. The tool for securing the positioning device to the bone of the patient comprises a screwdriver, and the stop of the tool for securing the positioning device is provided by a section of a shank of the screwdriver which is larger in diameter than the at least one cylindrical opening of the template. In such embodiments, the bone screw can with the aid of the screwdriver be screwed into the bone of the patient. Once the section of the screwdriver with the larger diameter abuts against the edge of the cylindrical opening of the template, the screwdriver can not further approach the bone of the patient, whereby the depth up to which the bone screw can be screwed into the bone is limited.

A device according to the invention for treating a bone of a patient in an implantation of a hip implant comprises a device for attaching a positioning device to a bone of a patient having some or all of the features described above and at least one bone milling device. The bone milling device comprises a receiving section for the guide section of the positioning device. The guide section is insertable into the receiving section. The receiving section is formed such that an axis of rotation of the bone milling device is aligned along the longitudinal axis of the guide section and the bone milling device is rotatable about the longitudinal axis of the guide section and is moveable along the longitudinal axis of the guide section when the guide section is inserted into the receiving section of the bone milling device.

By inserting the guide section of the positioning device into the receiving section of the bone milling device, the position of the bone milling device can be substantially defined in two axes which are perpendicular to the longitudinal direction of the guide section of the positioning device. Since the longitudinal axis of the guide section of the positioning device is aligned substantially along the longitudinal axis of the cylindrical opening of the template through which the positioning device has been attached to the bone of the patient, the position of the bone milling device relative to the trial hip implant and thereby also relative to the final hip implant can thus be defined in two axes. When milling the bone of the patient, the bone milling device can be moved along the longitudinal axis of the guide section toward the bone and then rotates, thereby removing bone of the patient.

In some embodiments, the receiving section of the bone milling device comprises a stop for the distal end of the positioning device. The depth to which the bone of the patient can be milled away can therewith be limited. Since, as stated above, the position of the distal end of the positioning device can be defined relatively accurate along the longitudinal direction of the cylindrical opening through which the positioning device is attached to the bone of the patient, the position of the region removed from the bone of the patient can therefore be defined in three axes.

A hip implant system according to the invention comprises a device for treating a bone of a patient with some or all of the features described above, a hip implant, and at least one augment that can be secured to the hip implant. The hip implant serves to receive an artificial joint socket and comprises a support surface for resting on the bone of the patient and having a shape corresponding to the shape of the support surface of the trial hip implant. The augment on a side facing away from the hip implant when the augment is secured to the hip implant comprises a surface having a shape corresponding to a shape of a treatment section of a bone milling device.

Since the shape of the support surface of the hip implant corresponds to the shape of the support surface of the trial hip implant, the final hip implant can be attached to the bone of the patient at substantially the same location and in the same orientation as previously the trial hip implant. It can due to the corresponding shapes of the side of the augment facing away from the hip implant and the treatment section of the bone milling device used be achieved that the shape of the section of the bone contacting the augment has a shape corresponding to the shape of the bone-contacting section of the augment. This causes relatively rapid adherence of the augment to the bone of the patient, with which the stability of the hip implant is enhanced.

In some embodiments, the template comprises several cylindrical openings. The hip implant system comprises several augments of different sizes. Every bone milling device has a treatment section having a generally spherical shape. Each augment is associated with one of the cylindrical openings of the template and a bone milling device. Each augment on the side facing away from the hip implant when the augment is secured to the hip implant has a generally spherical surface, where a radius of the generally spherical surface corresponds to a radius of the generally spherical treatment section of the bone milling device which is associated with the augment. A modular system is therewith provided that enables flexible adaptation of the hip implant systems to the condition of the bone of the patient and corresponding treatment of the bone of the patient during implantation of the hip implant.

A further device according to the invention for treating a bone of a patient during implantation of a hip implant comprises a template, a positioning device, and a tool. The template can at a predetermined position be secured to a trial hip implant and/or to the hip implant and comprises a first guide device. The positioning device can be secured to the bone and comprises a second guide device. The first and the second guide device are formed such that they interact with each other in such a manner when securing the positioning device to the bone that the positioning device is positioned relative to the template. The tool comprises a third guide device which is formed such that it interacts with the second guide device during treatment of the bone such that the tool is during treatment of the bone positioned relative to the positioning device.

BRIEF DESCRIPTION OF THE DRAWINGS

Embodiments of the invention are described hereafter with reference to the figures, where.

DETAILED DESCRIPTION OF THE INVENTION

Figure 1:
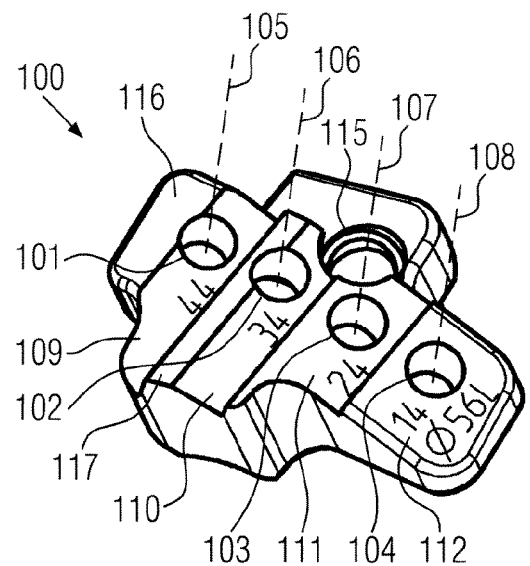
FIG. 1 shows a schematic view of a template.

FIG. 1 shows a schematic view of a template 100 which can be part of a device according to the invention.

Template 100 comprises several cylindrical openings 101, 102, 103, 104 which extend through template 100. FIG. 1 illustrates an embodiment of template 100 in which template 100 comprises four cylindrical openings 101, 102, 103, 104. In other embodiments, a larger number of cylindrical openings or a smaller number of cylindrical openings, for example, one, two or three cylindrical openings can be present.

Longitudinal axes of cylindrical openings 101, 102, 103, 104 are shown in FIG. 1 by dashed lines 105, 106, 107, 108. In some embodiments, longitudinal axes 105, 106, 107, 108 of cylindrical openings 101, 102, 103, 104 can be substantially parallel to each other. In other embodiments, longitudinal axes 105, 106, 107, 108 of cylindrical openings 101, 102, 103, 104 can be inclined relative to each other. Cylindrical openings 101, 102, 103, 104 can have substantially the same diameter so that elements interacting with openings 101, 102, 103, 104 when the device according to the invention is being used, such as drill guide 400 illustrated in FIG. 4, positioning device 600 illustrated in FIG. 6, and tool 700 illustrated in FIG. 7, can likewise be used with all cylindrical openings 101, 102, 103, 104 of template 100.

Cylindrical openings 101, 102, 103, 104 can be arranged in a row, where longitudinal axes 105, 106, 107, 108 of cylindrical openings 101, 102, 103, 104 are located substantially in one plane.

Template 100 can on one side have a stepped surface comprising several steps 109, 110, 111, 112. Cylindrical opening 101 extends through step 109, cylindrical opening 102 extends through step 110, cylindrical opening 103 extends through step 111, and cylindrical opening 104 extends through step 112. At least a portion of each of the steps 109, 110, 111, 112 can have a surface which is perpendicular to the longitudinal axis of the cylindrical opening extending through the respective step. In some embodiments, bevels can be present on some or all steps 109, 110, 111, 112. In the embodiment shown in FIG. 1, for example, step 109 comprises a bevel 116, and step 110 comprises a bevel 117, whereas no bevels are provided on steps 111, 112.

Figure 2:
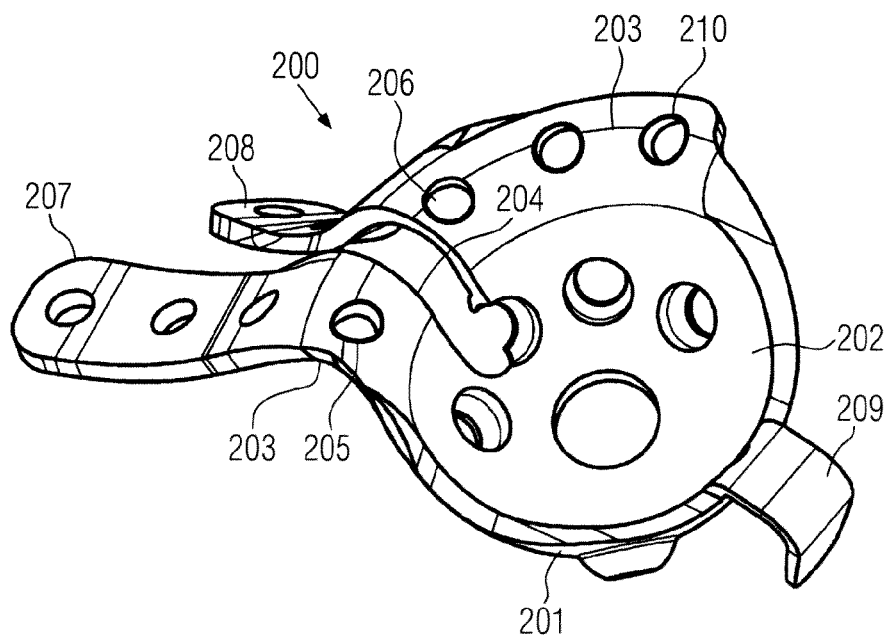
FIG. 2 shows a schematic view of a trial hip implant.

FIG. 2 shows a schematic view of a trial hip implant 200 that can be used together with template 100 shown in FIG. 1 and in combination with template 100 forms a device according to the invention. Trial hip implant 200 has a support surface 201 for resting on the bone of the patient. In the view of FIG. 2, large portions of support surface 201 are located on the side of trial hip implant 200 facing away from the viewer and are therefore covered. Portions of support surface 201 can in embodiments have a generally spherical shape, where a generally spherical shape is understood to be a shape that substantially corresponds to a spherical surface or a part of a spherical surface, where deviations from an ideal spherical shape such as a certain roughness, openings and/or indentations can be present.

Trial hip implant 200 comprises a section 202 having a general shape of a spherical dome shell, located on the outer side of which is that portion of support surface 201 having the generally spherical shape. In addition, trial hip implant 200 comprises an edge section 203 to which plates 207, 208 can be attached. A hook 209 which can be hooked into the hip bone of the patient can be attached to trial hip implant 200 on the side facing away from plates 207, 208. Bores, one of which is by way of example provided with reference numeral 210, can be provided in section 202 having the general shape of a spherical dome shell, in edge section 203 and in plates 207, 208. Screws can be guided through bores 210 with which trial hip implant 200 can be fixed to the hip bone of the patient.

The above described features of trial hip implant 200 can substantially correspond to the features of a final hip implant which is permanently implanted into a patient.

In addition to the features described above, trial hip implant 200 can comprise a slit-shaped notch 204 extending through edge section 203 and into section 202 having the general shape of a spherical dome shell. In embodiments in which trial hip implant 200 comprises plates 207, 208, slit-shaped notch 204 can open into the gap between plates 207, 208. No element corresponding to slit-shaped notch 204 needs to be present on the final hip implant which is implanted into the patient, whereby the final hip implant can be more stable as compared to trial hip implant 200. The final hip implant can comprise yet further features that differ from those of trial hip implant 200. The final hip implant can in some embodiments be a hip implant of the type described in WO 2007/118708 A2.

Figure 3:
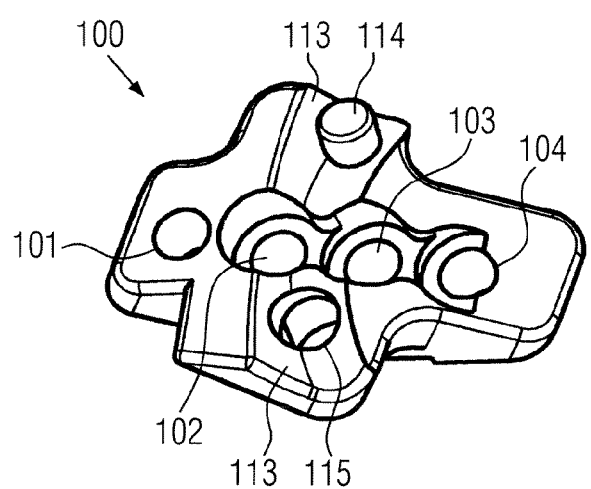
FIG. 3 shows a schematic view of the template shown in FIG. 1 in which the side of the template which in the view of FIG. 1 faces away from the viewer is visible.

FIG. 3 shows a view of template 100 shown in FIG. 1 from a different perspective from which the side of implant 100, that is facing away from the viewer in the illustration of FIG. 1, is visible. On that side, implant 100 has a surface with a section 113 which has a shape that is complementary to edge section 203 of trial hip implant 200 and can rest on edge section 203 of trial hip implant 200. The side, in the illustration of FIG. 3 facing the viewer, on which section 113 is located faces trial hip implant 200 and the side of template 100 visible in FIG. 1 on which steps 109, 110, 111, 112 are located faces away from trial hip implant 200.

Template 100 is adapted to be secured to trial hip implant 200 in the position described above. For this purpose, template 100 can comprise an opening 115 that is separate from cylindrical openings 101, 102, 103, 104 and in flush alignment with a threaded opening 206 in edge section 203 of trial hip implant 200 when section 113 of the surface of template 100 rests on edge section 203 of trial hip implant 200. A screw with an external thread that is complementary to the internal thread of threaded opening 206 in edge section 203 of trial hip implant 200 can be guided through opening 115 of template 100 and screwed into threaded opening 206, whereby template 100 is fixed detachably to trial hip implant 200.

An opening 205 can be located in edge section 203 of trial hip implant 200 on the side of slit-shaped notch 204 opposite threaded opening 206. A protrusion 114 can be located on template 100 and be complementary to opening 205 in edge section 203 of trial hip implant 200 and engage with opening 205 when section 113 of the surface of the template rests on edge section 203 of trial hip implant 200. Rotation of template 100 relative to trial hip implant 200 can be prevented by projection 114 and opening 205.

When template 100 is secured to trial hip implant 200, as described above, cylindrical openings 102, 103, 104 of template 100 are disposed opposite to slit-shaped notch 204 of the trial hip implant, whereas cylindrical opening 101 of template 100 is disposed opposite to a gap between plates 207, 208 of trial hip implant 200. The widths of slit-shaped notch 204 and the gap between plates 207, 208 adjoining slit-shaped notch 204 can be larger than the diameter of cylindrical openings 101, 102, 103, 104, so that any straight line extending through one of the cylindrical openings 101, 102, 103, 104 and being parallel to the longitudinal axis 105, 106, 107 and 108, respectively, of the respective cylindrical opening extends through slit-shaped notch 204 or the gap between plates 207, 208 without intersecting trial hip implant 200. Consequently, a cylindrical object having a diameter corresponding to the diameter of cylindrical openings 101, 102, 103, 104 can be passed through each of the cylindrical openings 101, 102, 103, 104 and the gap between plates 207, 208 or the slit-shaped notch 204 of trial hip implant 200, respectively, without striking against trial hip implant 200. This applies in particular to positioning device 600 described below in more detail with reference to FIG. 6, which comprises a cylindrical guide section 601.

Figure 4:
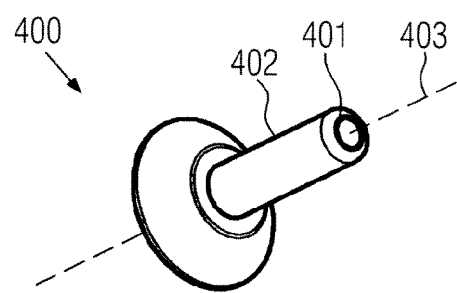
FIG. 4 shows a schematic view of a drill guide according to the invention.
Figure 5:
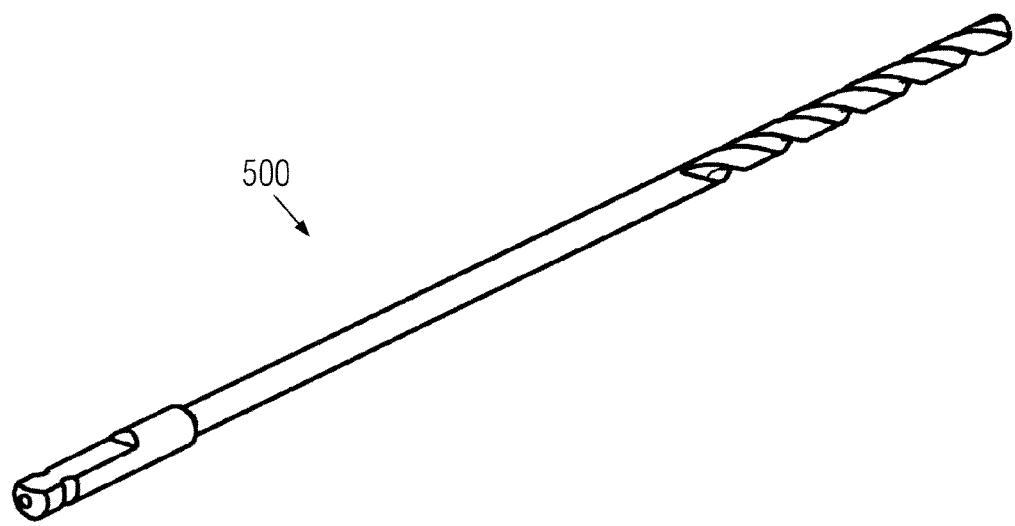
FIG. 5 shows a schematic view of a bone drill bit.

FIG. 4 shows a drill guide 400. The drill guide comprises a cylindrical section 402 having a diameter corresponding to the diameter of cylindrical openings 101, 102, 103, 104 of template 100. Cylindrical section 402 of drill guide 400 can therefore be inserted through any of the cylindrical openings 101, 102, 103, 104 of template 100, where a longitudinal axis 403 of cylindrical section 402 of drill guide 400 is aligned with the longitudinal axis of the respective cylindrical opening of template 100. Drill guide 400 comprises a channel 401 which extends along longitudinal axis 403 of cylindrical section 402. A bone drill bit 500 shown in FIG. 5 can be guided through channel 401. Bone drill bit 500 can be aligned along longitudinal axis 403 of channel 401 of the drill guide, and thereby also along the longitudinal axis of the cylindrical opening of template 100 into which drill guide 400 is inserted. Drill guide 400 and bone drill bit 500 can be used for pre-drilling a bone of a patient when attaching a positioning device 600, which shall hereafter be described with reference to FIG. 6.

Positioning device 600 is a bone screw with a thread 604 and a cylindrical guide section 601. A diameter of cylindrical guide section 601 can correspond to a diameter of cylindrical openings 101, 102, 103, 104 of template 100, and an outer diameter of thread 604 can be smaller than or equal to the diameter of guide section 601, so that positioning device 600 can be passed through any of the cylindrical openings 101, 102, 103, 104. While guide section 601 is located in one of the cylindrical openings 101, 102, 103, 104 of template 100, longitudinal axis 602 of cylindrical guide section 601 is aligned along the longitudinal axis of the respective cylindrical opening. Positioning device 600 can thereby be moved along the longitudinal axis of the cylindrical opening and rotated about the longitudinal axis of the cylindrical opening. The orientation of longitudinal axis 602 of positioning device 600 and the position of guide device 600 in two axes which are perpendicular to the longitudinal axis of the cylindrical opening in which guide section 601 is located, however, are defined relative to template 100. When template 100 is secured to trial hip implant 200, also the position of positioning device 600 is defined in two axes relative to trial hip implant 200.

Provided at a distal end 603 of positioning device 600, which is located on a side of guide section 601 of positioning device 600 facing away from thread 604, is a drive profile, for example, a hexagon recess.

Figure 7:
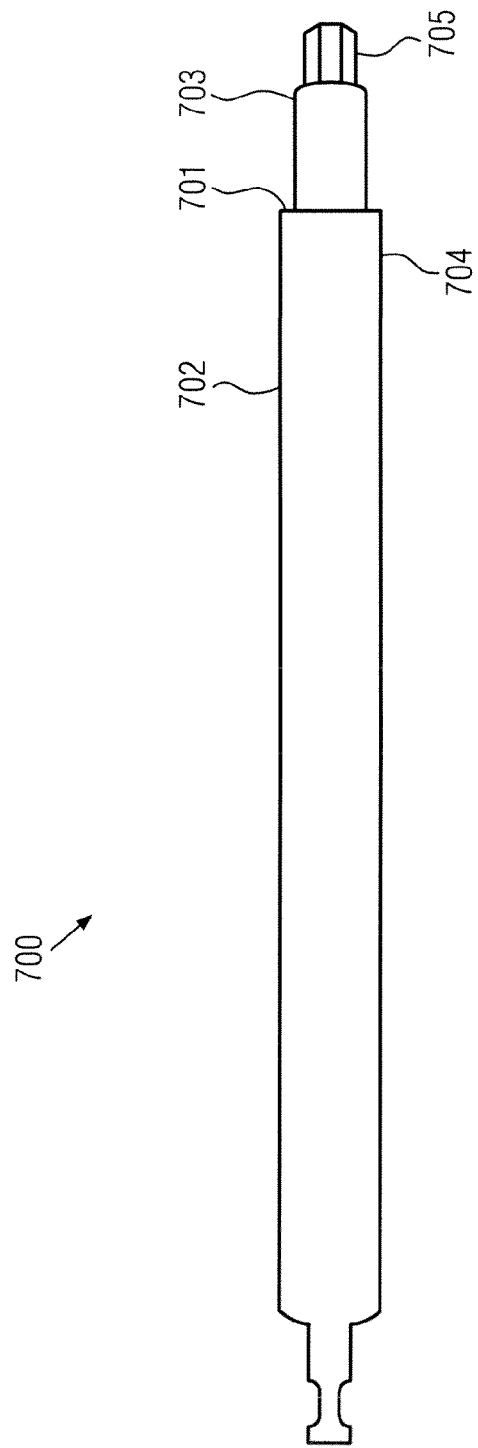
FIG. 7 shows a schematic view of a tool for securing the positioning device shown in FIG. 6 to a bone.

FIG. 7 shows a view of a tool 700 that can be used to screw thread 604 of positioning device 600 into the hip bone of a patient, while guide section 601 of positioning device 600 is passed through one of the cylindrical openings 101, 102, 103, 104 of template 100. Tool 700 is a screwdriver with a shank 704 and a blade 705 which has a shape corresponding to the drive profile at distal end 603 of positioning device 600. Adjoining blade 705 is a portion 703 of shank 704 having a cylindrical shape and a diameter corresponding to the diameter of cylindrical openings 101, 102, 103, 104 of template 100. Shank 704 of tool 700 also comprises a section 702 having a larger diameter than cylindrical openings 101, 102, 103, 104 and providing a stop 701 for tool 700.

If positioning device 600 is screwed through one of the openings 101, 102, 103, 104 of template 100 into the bone of the patient, section 703 of shank 704 of tool 700 is first inserted into the opening used, until finally stop 701 abuts against that one of steps 109, 110, 111, 112 of template 100 in which the opening is located. The depth is therewith defined to which positioning device 600 is screwed into the bone of the patient and thereby the position of distal end 603 of the positioning device relative to template 100 in the axis that is parallel to the longitudinal axis of the opening of the template used. By attaching positioning device 600 to the bone of the patient through one of the openings 101, 102, 103, 104 of template 100 by use of tool 700, the position of distal end 603 of the positioning device secured to the bone of the patient can be defined in three axes relative to trial hip implant 200 to which template 100 is secured.

When template 100 as shown in FIGS. 1 and 3 comprises several cylindrical openings 101, 102, 103, 104, there are several ways to attach positioning device 600 to the bone of the patient at a defined position relative to trial hip implant 200.

Figure 8:
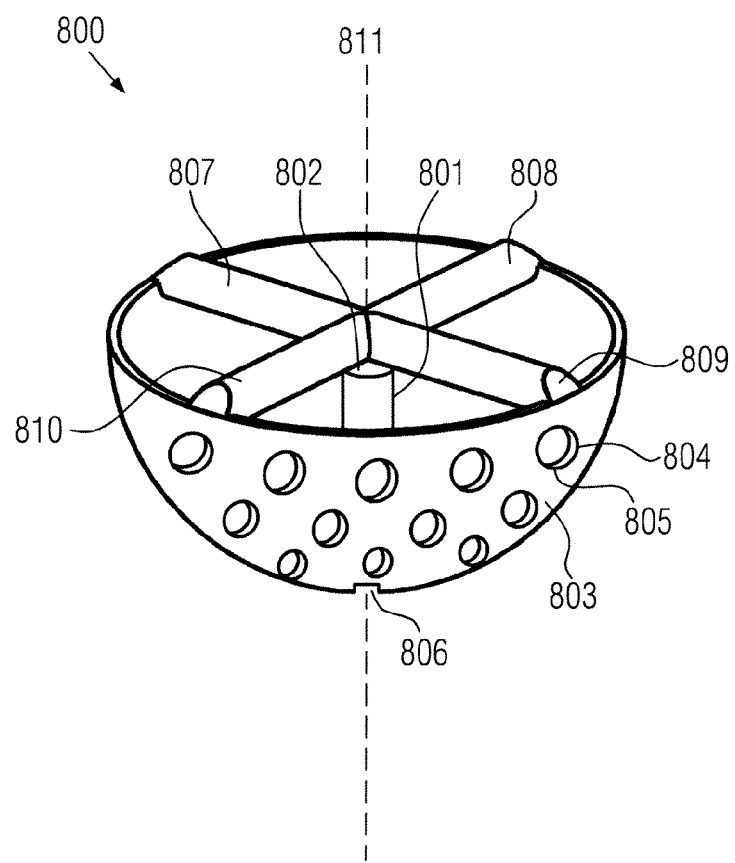
FIG. 8 shows a schematic view of a bone milling device.

Positioning device 600 as described above attached at a defined position relative to trial hip implant 200 to the bone of the patient can be used in embodiments of the invention to guide a bone milling device 800, which is illustrated in FIG. 8.

Bone milling device 800 comprises a treatment section 803. Treatment section 803 can have a generally spherical shape. For example, treatment section 803 can, as shown in FIG. 8, have a substantially semi-spherical shape. Treatment section 803 can comprise several blades, one of which is by way of example denoted by reference numeral 804. Openings can be located beside the blades. The opening which is beside blade 804 is in FIG. 8 by way of example denoted with reference numeral 805. Bone chips that are removed by the blades can through the openings enter into the interior of treatment section 803, so that they can after completion of the treatment of the bone be removed together with the bone milling device 800.

Bone milling device 800 comprises a receiving section 801 for guide section 601 of positioning device 600. Receiving section 801 can have a hollow cylindrical shape and extend from an opening 806 at the pole of treatment section 803 in a direction towards the center of treatment section 803.

Located at one end of receiving section 801 facing away from opening 806 is a stop 802 for distal end 603 of positioning device 600. Bone milling device 800 can also comprise strut members 807, 808, 809, 810 at which bone milling device 800 can be engaged by a tool for rotating bone milling device 800. In doing so, one milling device 800 rotates about a longitudinal axis 811 of receiving section 801.

An inner diameter of receiving section 801 of the bone milling device can correspond to a diameter of guide section 601 of positioning device 600. Guide section 601 of positioning device 600 attached to the bone of the patient can be inserted into receiving section 801 of bone milling device 800 and the bone of the patient can be treated by rotating bone milling device 800 about longitudinal axis 811 of receiving section 801. During treatment, bone milling device 800 can be moved toward the bone, where guide section 601 of the positioning device further penetrates into receiving section 801 of bone milling device 800 until distal end 603 of positioning device 600 abuts stop 802. Movement of bone milling device 800 toward the bone of the patient and thereby the removal of bone material by bone milling device 800 is thereby substantially terminated.

By using bone milling device 800 in combination with positioning device 600, bone material of the patient can thus be removed from a substantially spherical region which is defined by the size of treatment section 803, the arrangement of stop 802 relative to treatment section 803, and the position of distal end 603 of positioning device 600. Since, as explained above, the position of distal end 603 of positioning device 600 can be defined by attaching positioning device 600 to the bone of the patient by use of template 100 attached to trial hip implant 200 and tool 700 relative to trial hip implant 200, bone material of the patient can with the above-described milling process be removed from a region which is located at a defined position relative to trial hip implant 200.

Figure 9A:
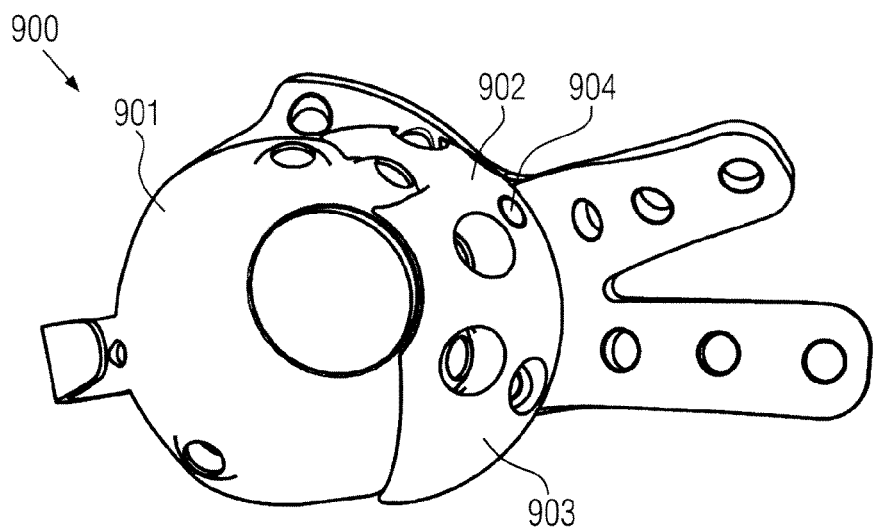
FIG. 9A shows a schematic view of a hip implant with an augment secured thereto.
Figure 9B:
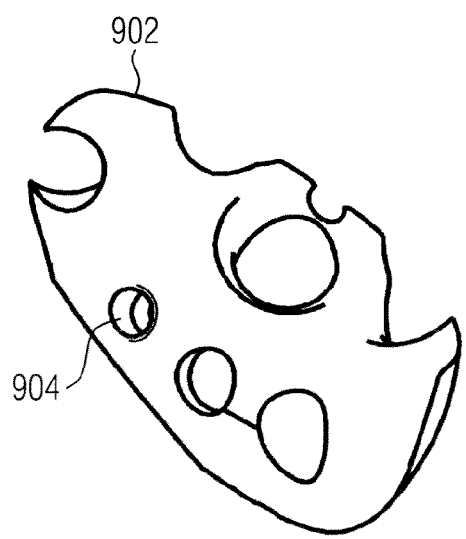
FIG. 9B shows a schematic view of the augment shown in FIG. 9A from a different perspective.

FIG. 9A shows a view of a hip implant 900 to which an augment 902 is secured by use of a screw 904. Hip implant 900 is adapted to receive an artificial joint socket of a patient and comprises a support surface 901 for resting on a bone of the patient. The shape of support surface 901 corresponds to the shape of support surface 201 of trial hip implant 200, so that hip implant 900 can after removal of trial hip implant 200 be secured to the bone of the patient substantially at the same position as was previously trial hip implant 200. Further features of hip implant 900 can correspond to those of the hip implant described in WO 2007/118708 A2.

Augment 902 can in some embodiments be manufactured from metal powder by means of a sintering process, whereby it is given a porous structure that promotes ingrowth of the bone of the patient into augment 902. The metal powder can be composed substantially of pure titanium or a titanium alloy.

Augment 902 can on a side facing away from hip implant 900 when augment 902 is secured to hip implant 900 and in the view of FIG. 9A facing the viewer comprise a surface 903 having a shape corresponding to a shape of a treatment section 803 of a bone milling device 800. In particular, surface 903 of augment 902 can on the side facing away from hip implant 900 have a generally spherical shape, where the radii of generally spherical surface 903 of augment 902 and processing section 803 of bone milling device 800 can correspond to one another. For example, the radius of generally spherical surface 903 of augment 902 can be slightly smaller than or approximately equal to the radius of treatment section 803 of bone milling device 800.

By treatment of the bone of the patient by use of the device described above with reference to FIGS. 1 to 8, the bone of the patient can be treated such that the generally spherical surface 903 of augment 902 after securing hip implant 900 to the bone of the patient rests against or is in close proximity to the bone. Unnecessary removal of bone material is thereby avoided and a rapid adhesion of augment 902 to the bone is enhanced.

A hip implant system according to the invention can comprise several hip implants similar to hip implant 900 shown in FIG. 9A. Hip implants of different sizes can be provided to allow for the adaptation to the individual anatomy of a patient. For example, the hip implant system can contain hip implants comprising sections having the general shape of a spherical dome shell of different diameters. For example, diameters of the section having the general shape of a spherical dome shell of approximately 48 mm, approximately 52 mm, approximately 56 mm, approximately 60 mm and approximately 64 mm can be provided. In addition, different hip implants of any size can be provided for replacement of the left hip joint and the right hip joint, where hip implants for replacement of the left hip joint are in mirror-symmetry to those for replacement of the right hip joint. A corresponding sample implant can be provided for each of the different hip implants and have features corresponding to those of trial hip implant 200 described above with reference to FIG. 2. It can by using the sample implant be tested which of the hip implants fits best to the individual anatomy of the patient.

Augments of different sizes can be available for each of the different hip implants. For example, four different augments can be present for every hip implant.

A separate template can be provided for each of the trial hip implants and have features corresponding to template 100 described above with reference to FIGS. 1 and 3, where the templates can have different dimensions according to the different dimensions of the trial hip implants. The number of cylindrical openings of a template corresponds to the number of different augments that are provided for the hip implant that corresponds to the sample implant. For example, in embodiments in which four different augments are provided for every hip implant, the templates associated with the respective sample implant can comprise four cylindrical openings, as shown in FIGS. 1 and 3. The template can, as shown in FIG. 1, have markings that indicate the hip implant with which the template is associated, as well as the augments with which the individual cylindrical openings of the template are associated.

The hip implant system can additionally comprise bone milling devices of different sizes, where each of the augments is associated with a bone milling device that matches in terms of dimensions.

Figure 6:
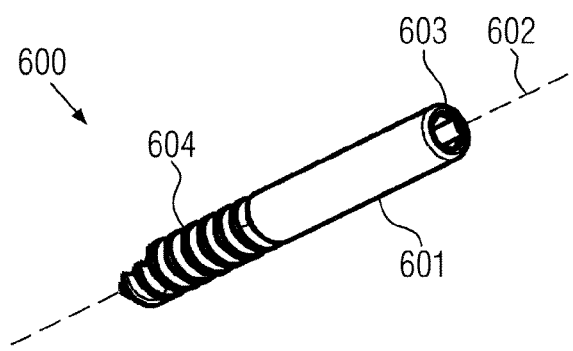
FIG. 6 shows a schematic view of a positioning device.

The hip implant system can also comprise positioning devices of different sizes similar to positioning device 600 shown in FIG. 6 which differ in the length of thread 604. A positioning device can thereby—as described in more detail below—be selected having a size that is suitable for the individual anatomy of the patient, so that, firstly, bicortical attachment of positioning device 600 to the bone can be achieved, but secondly, the tip of thread 604 does not protrude out too far from the bone, which could lead to injury of the tissue of the patient.

The application of the above-described components of a device according to the invention is described herebelow with reference to FIGS. 10A to 10G. Some reference numerals have for reasons of clarity been omitted in FIGS. 10A to 10G.

Figure 10A:
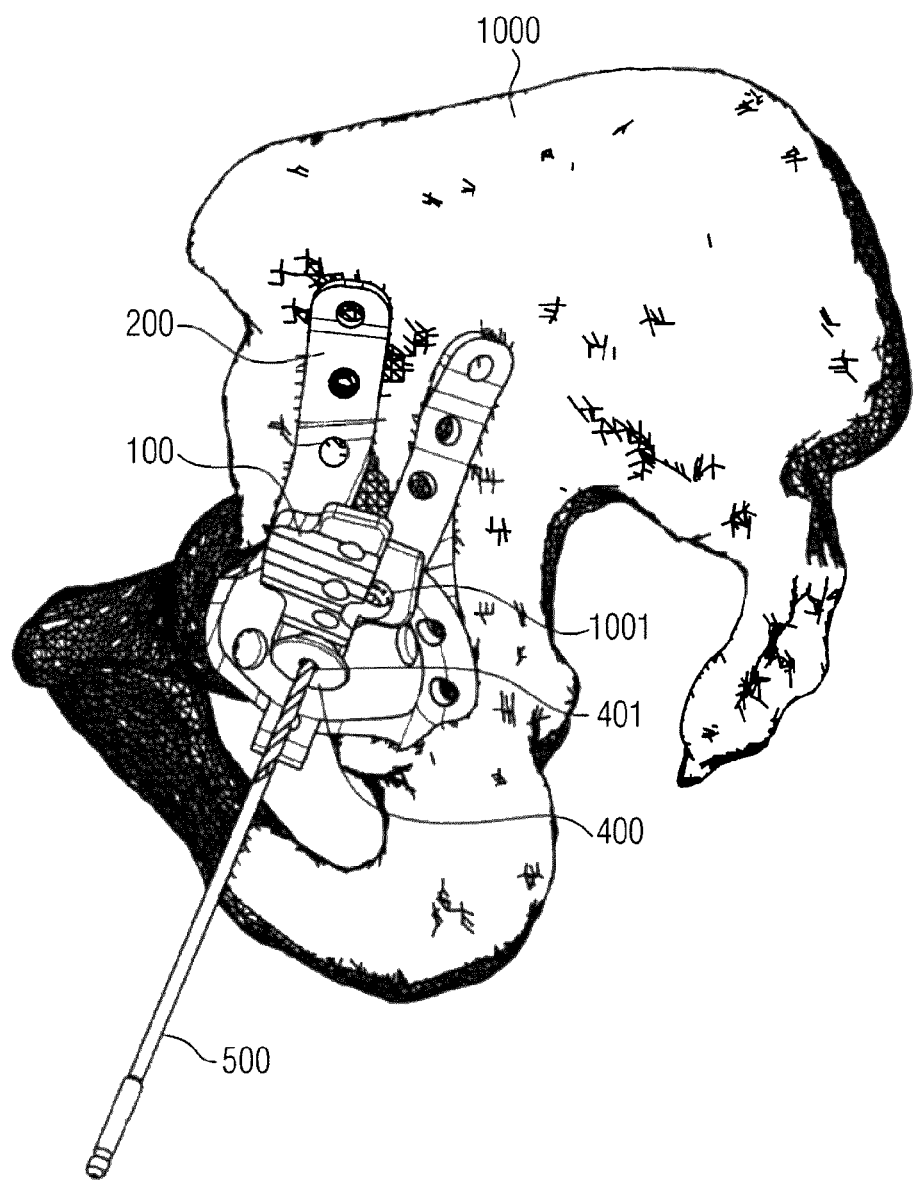
FIGS. 10A-10G show schematic views of a hip bone during treatment by use of a device according to the invention.

FIG. 10A shows a view of a hip bone 1000 of a patient to which trial hip implant 200 described above with reference to FIG. 2 is attached. In order to avoid trial hip implant 200 from shifting, trial hip implant 200 can be fixed to bone 1000 by use of a bone screw guided through one of the openings 210 of trial hip implant 200. Prior to attaching trial hip implant 200 to bone 1000, known measures can be performed to prepare bone 1000, for example, the acetabulum can be initially milled with a bone milling device 800 similar to the one shown in FIG. 8.

After attaching trial hip implant 200 to bone 1000, template 100 can be secured to trial hip implant 200 by use of a screw 1001 passed through opening 115 of template 100 and screwed into threaded opening 206 of trial hip implant 200.

Before or after securing template 100 to trial hip implant 200, a size of an augment that fits to the patient can be determined. In some embodiments, markings can for this purpose be applied to trial hip implant 200 which correspond to the contours of the differently sized augments. Selecting an appropriate augment size can then be done by comparing the markings on the trial hip implant with the defects existing on bone 1000.

Drill guide 400 can subsequently be inserted into that one of the cylindrical openings 101, 102, 103, 104 of template 100 which is associated with the augment size selected. Drill guide 400 is in FIG. 10A shown as being inserted into cylindrical opening 104 of template 100. Bone 1000 can then be pre-drilled by use of bone drill 500. For this purpose, bone drill 500 can be inserted into channel 401 of drill guide 400 and be made to rotate by use of a drive, not shown in FIG. 10A. The drilling operation can be continued until drill bit 500 exits bone 1000 on the side opposite to trial hip implant 200. Drill guide 400 and bone drill 500 can then be removed.

Figure 10B:
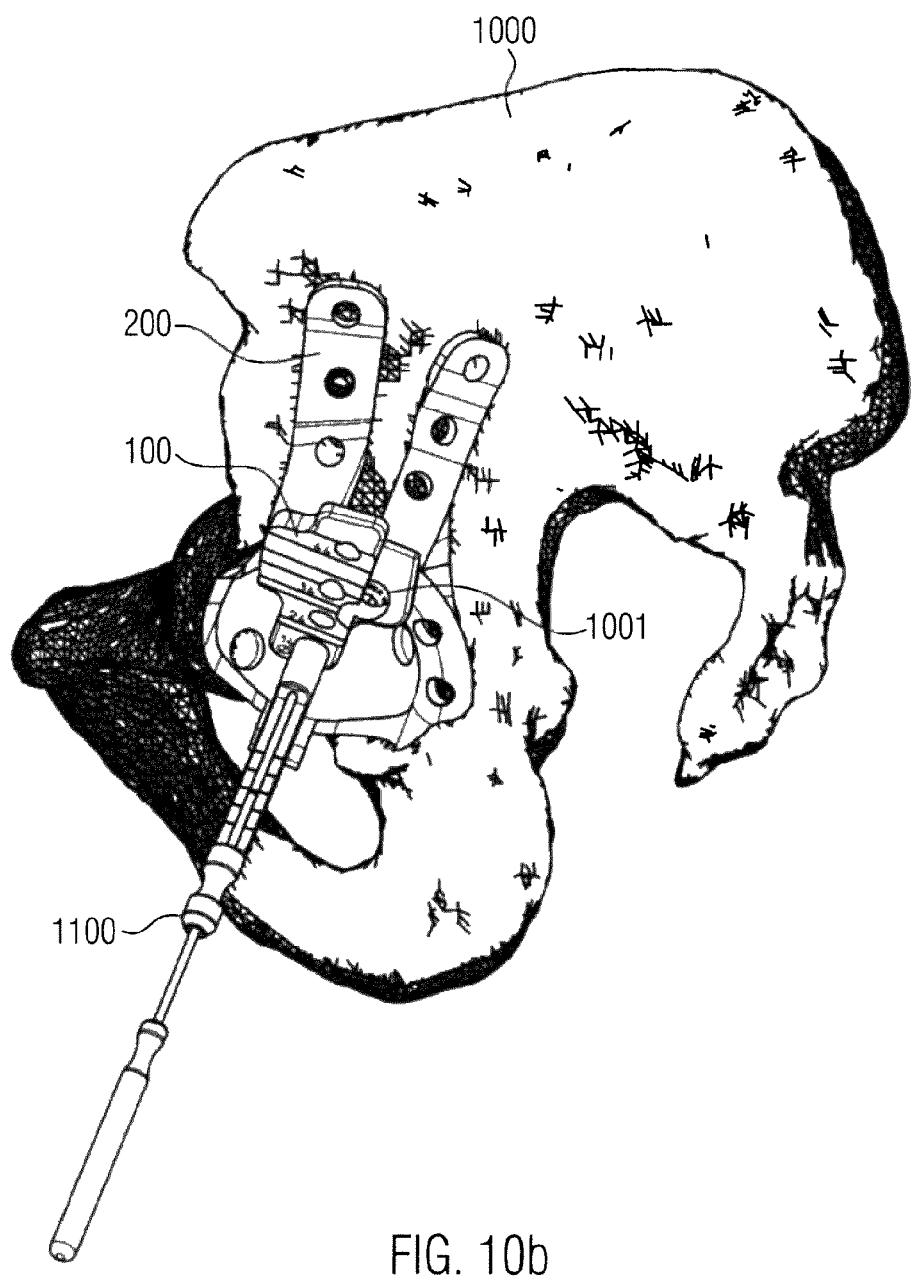
Figure 11:
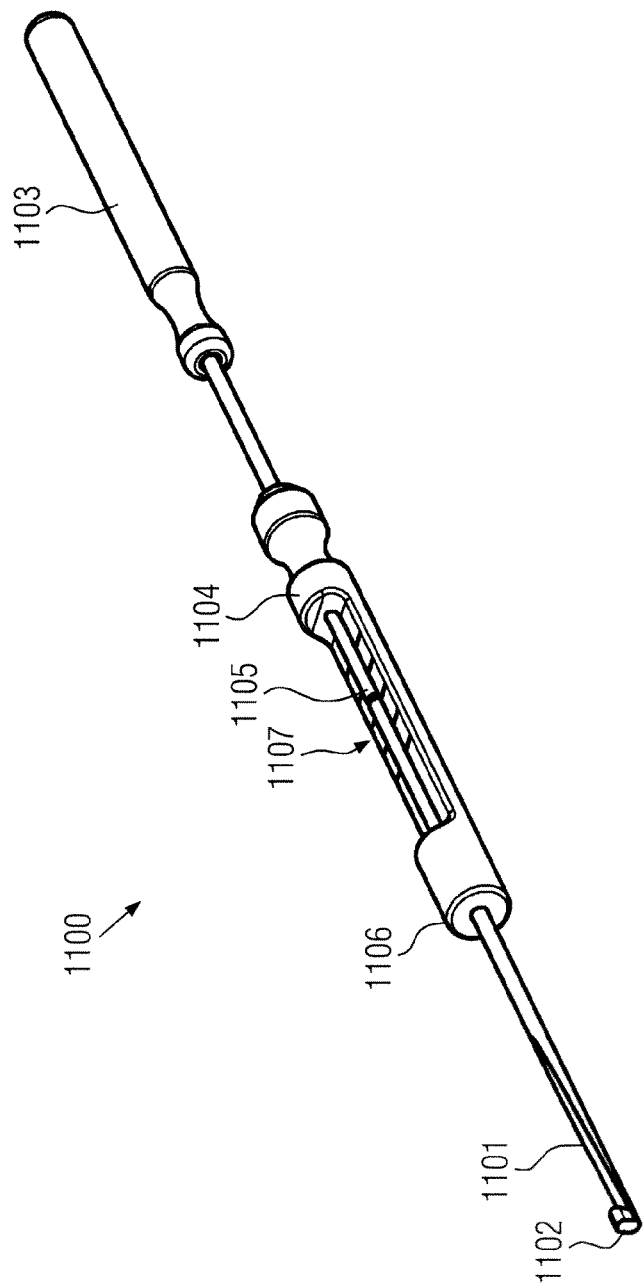
FIG. 11 shows a schematic view of a measuring device for determining the length of the positioning device to be used.

Thereafter, as shown in FIG. 10B, a size of positioning device 600 which is suitable for the patient can then be determined. A depth gauge 1100 can for this purpose be used which is shown in FIG. 11 in more detail.

Depth gauge 1100 comprises a slider 1101 with a marking 1105. A hook 1102 is disposed at one end of slider 1101. A handle 1103 is disposed at the other end of slider 1101. Depth gauge 1100 also comprises a rod 1104 with a stop 1106 to rest on steps 109, 110, 111, 112 of template 100. A scale 1107 is attached to rod 1104. Slider 1101 can by operating handle 1103 be moved along rod 1104 and a reading for the distance between hook 1102 and stop 1106 can be taken with the aid of marking 1105 and scale 1107.

For determining the required size of positioning device 600, the end of slider 1101, facing away from handle 1103 and at which hook 1102 is disposed, can be introduced into the cylindrical opening of template 100 associated with the selected augment size. In the example shown in FIG. 10B, this is cylindrical opening 104. The stop 1106 of rod 1104 is thereafter fixed to step 112 corresponding to the cylindrical opening, and the side of bone 100 located opposite trial hip implant 200 is searched for with hook 1102 by moving the slider 1101 by use of handle 1103. The distance of the opposite side of bone 1000 from step 112 can then be determined by reading the position of marking 1105 relative to scale 1107. A positioning device 600 having a length matching the measured value suitable for achieving a bicortical fixation can then be selected.

Figure 10C:
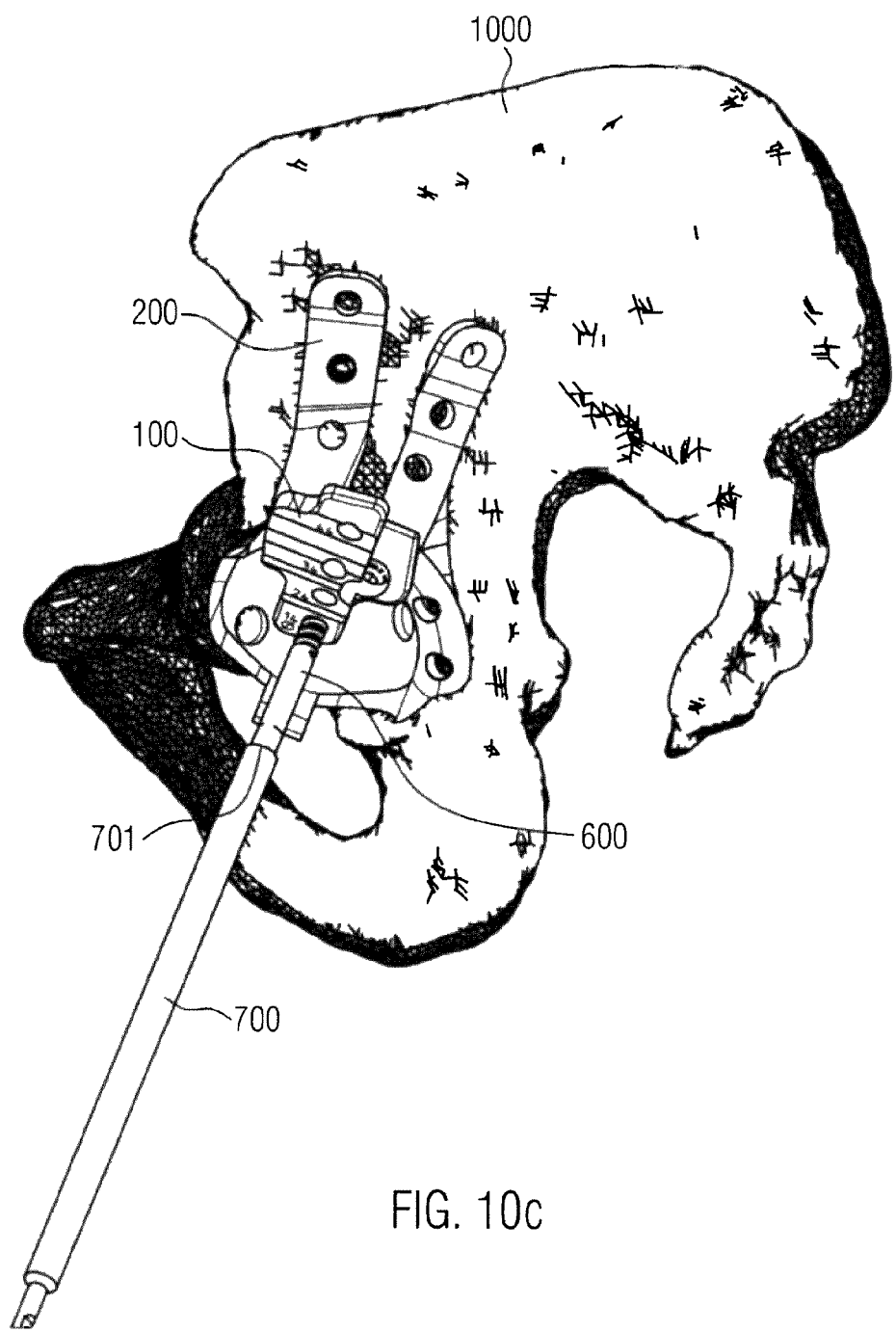
Figure 10D:
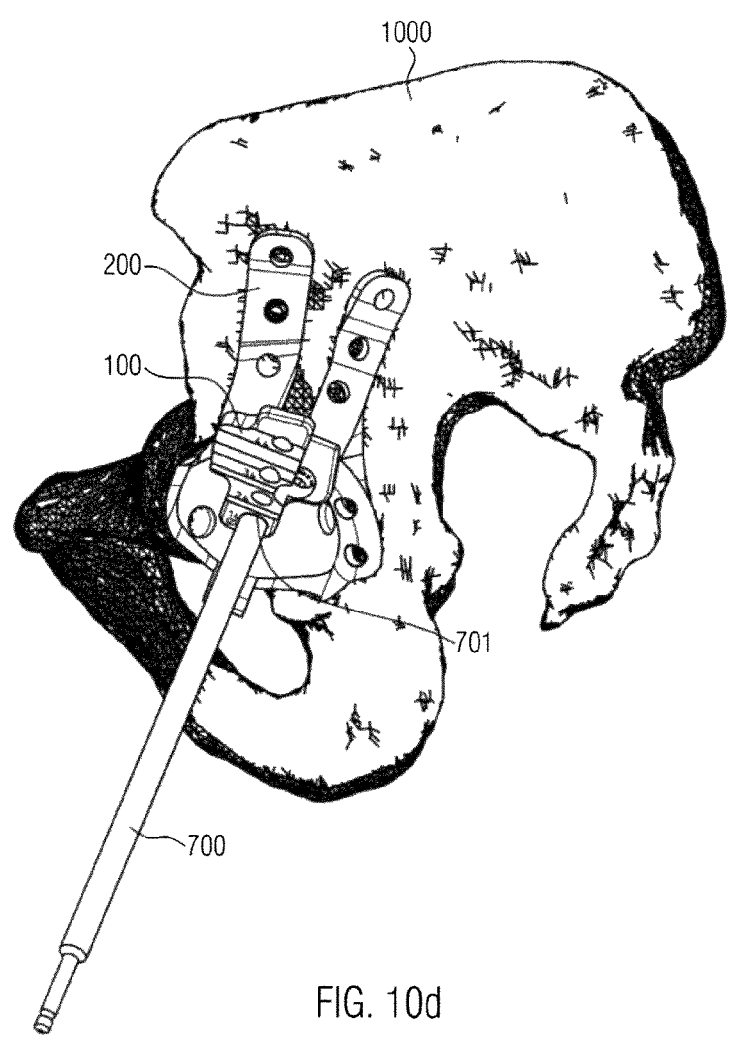
Figure 10E:
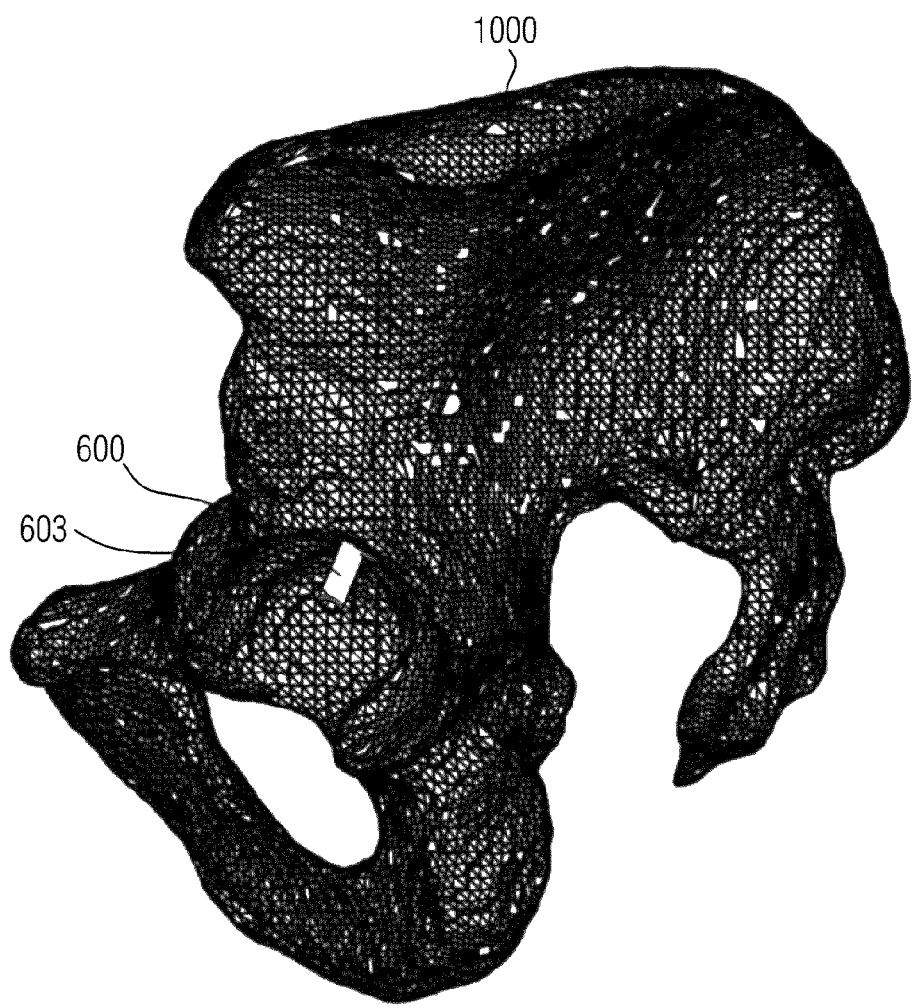

Subsequently, as shown in FIG. 10C, positioning device 600 can be inserted into cylindrical opening 104 associated with the selected augment size and screwed into bone 1000 by use of tool 700. For this purpose, tool 700 can be made to rotate by use of a drive, not shown in FIG. 10C. Positioning device 600 can continue to be screwed in until stop 701 of tool 700 abuts step 112 of template 100 through which cylindrical opening 104 associated with the selected augment size extends, as shown in FIG. 10D. Distal end 603 of positioning device 600 is then located relative to trial hip implant 200 at a position that is determined by the geometry of trial hip implant 200, template 100, and tool 700. Since positioning device 600 is screwed to bone 1000, distal end 603 of positioning device 600 remains at this position, when—as shown in FIG. 10E—trial hip implant 200 and template 100 are removed once positioning device 600 has been attached to the bone.

Figure 10F:
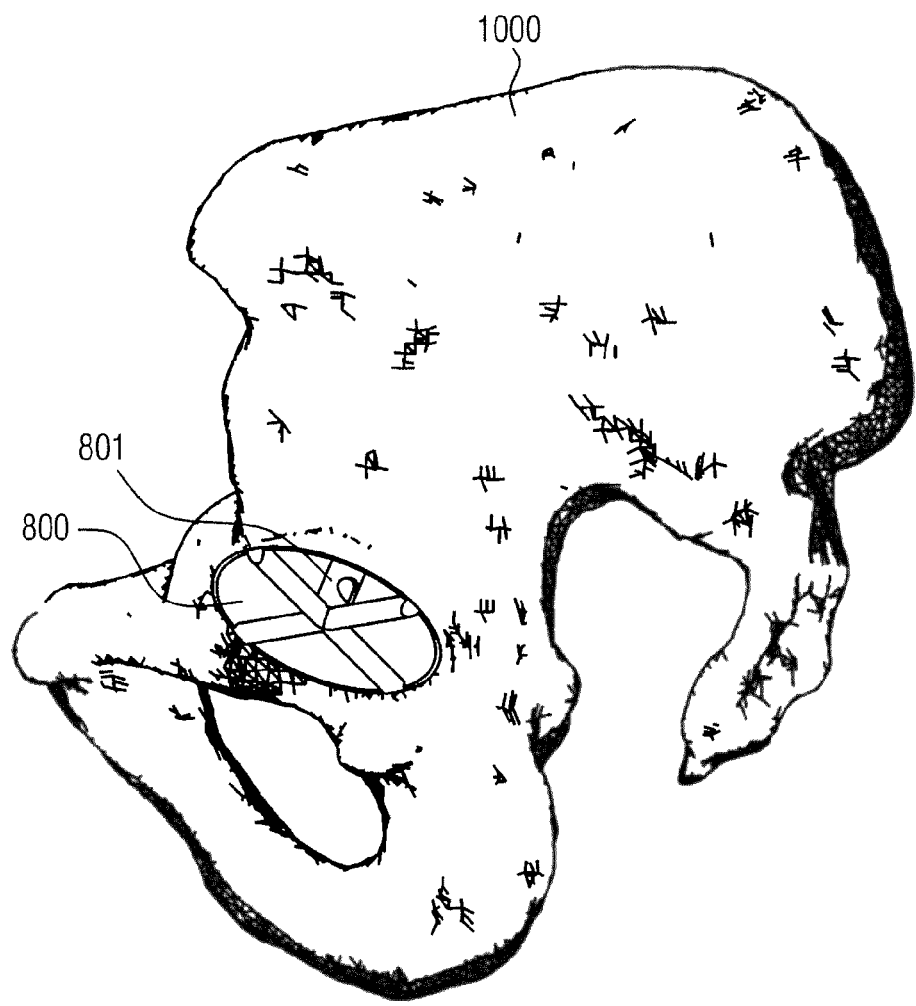

Subsequently, as shown in FIG. 10F, bone 1000 can be treated by use of bone milling device 800, where, in the case of several bone milling devices of different size, the bone milling device associated with the selected augment size is used. Guide section 601 of positioning device 600 is inserted through opening 806 at the pole of treatment section 803 into receiving section 801 of bone milling device 800. Bone milling device 800 can then be made to rotate by use of a drive, not shown in FIG. 10F, whereby material is removed from bone 1000 until distal end 603 of the positioning device abuts against stop 802 of bone milling device 800, whereby further removal of bone material by bone milling device 800 is prevented.

Figure 10G:
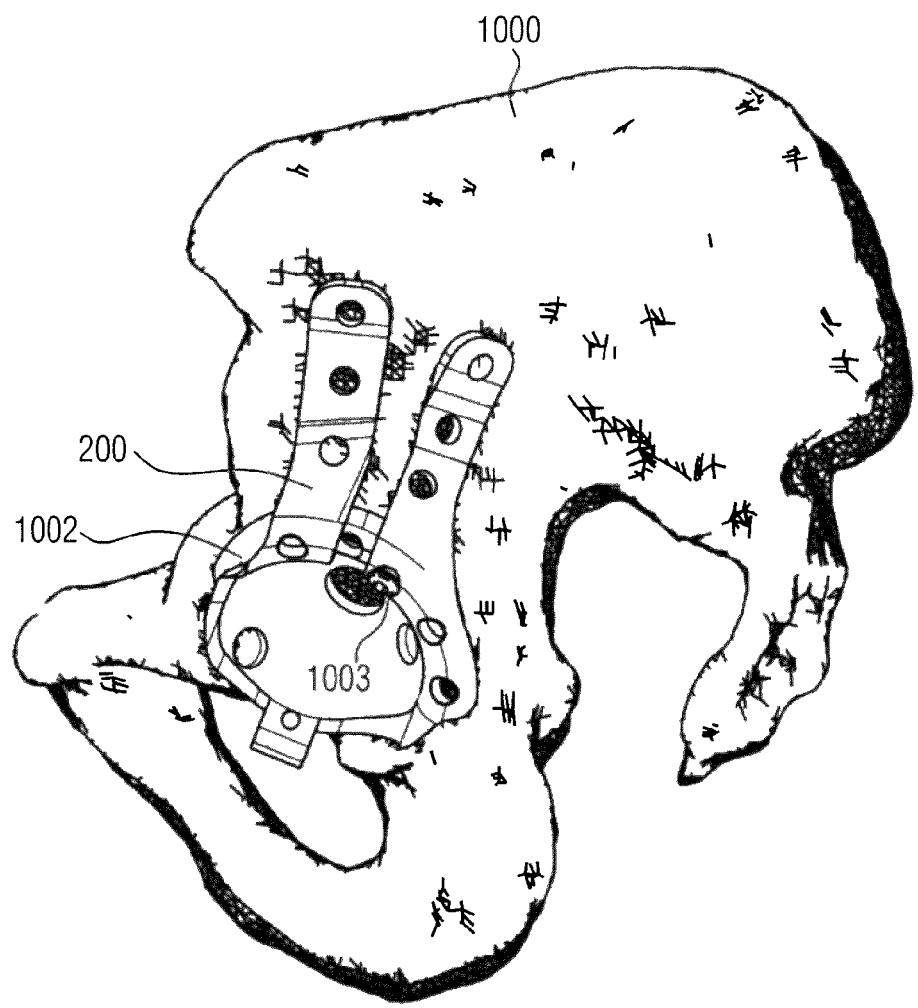

Positioning device 600 can subsequently be unscrewed from bone 1000, and it can then be verified, as illustrated in FIG. 10G, by use of trial hip implant 200 and a sample augment 1002 attached with screw 1003 to trial hip implant 200 and having substantially the same shape as the final augment of the size selected, whether correct positioning of the final hip implant with the final augment to bone 100 can be achieved. If this is the case, then the final hip implant and the final augment can be secured to bone 1000 of the patient.

What is claimed is:

1. A device for attaching a positioning device to a bone of a patient at a predetermined position relative to a hip implant comprising:
    a trial hip implant with a support surface for resting on said bone of the patient; and
    a template that can be secured to said trial hip implant and has at least one cylindrical opening with a longitudinal axis;
    wherein said trial hip implant is shaped such that any straight line which runs through one of said at least one cylindrical opening and is parallel to said longitudinal axis of a respective said at least one cylindrical opening does not intersect said trial hip implant when said template is secured to said trial hip implant;
    wherein said trial hip implant comprises a section having a general shape of a spherical dome shell and an edge section, and said template on one side facing said trial hip implant when said template is secured to said trial hip implant has a surface with a section having a shape that is complementary to said edge section;
    wherein said trial hip implant has a slit-shaped notch that extends through said section having the general shape of a spherical dome shell and said edge section, wherein it is for at least one of said cylindrical openings true that any straight line extending through said opening and being parallel to the longitudinal axis of said opening extends through said slit-shaped notch when said template is secured to said trial hip implant; and
    wherein said device additionally comprises a drill guide which is insertable through said at least one cylindrical opening of said template when said templet is secured to said trial hip implant and comprises a channel through which a bone drill can be guided.

2. The device according to claim 1, wherein said template comprises several cylindrical openings that are arranged in a row.

3. The device according to claim 2, wherein said longitudinal axes of said several cylindrical openings are parallel to each other.

4. The device according to claim 1, wherein:
    said trial hip implant on a first side of said slit-shaped notch comprises an opening in said edge section and said template comprises a protrusion that is complementary to said opening in said edge section and engages in said opening in said edge section when said template is secured to said trial hip implant;
    said trial hip implant on a second side of said slit-shaped notch being disposed opposite to said first side comprises a threaded opening in said edge section having an internal thread, and said template comprises an opening that is separate from said several cylindrical openings and is flush with said threaded opening in said edge section when said template is secured to said trial hip implant; and
    said device additionally comprises a screw with an external thread that is complementary to said internal thread in said threaded opening in said edge section of said trial hip implant for screwing said template to said trial hip implant.

5. The device according to 1, additionally comprising a positioning device wherein said positioning device comprises a cylindrical guide section having a longitudinal axis which can be guided through said at least one cylindrical opening of said template; wherein said guide section is moveable relative to said template along said longitudinal axis of said at least one cylindrical opening and said longitudinal axis of said guide section is aligned along said longitudinal axis of said at least one cylindrical opening.

6. The device according to claim 5, additionally comprising a tool for securing said positioning device to said bone of the patient through one of said at least one cylindrical opening of said template; wherein said tool comprises a stop for defining a distance between a distal end of said positioning device secured to said bone of the patient and an end of said cylindrical opening of said template that faces away from said trial hip implant through which said positioning device is secured to said bone of the patient.

7. The device according to claim 6, wherein said positioning device comprises a bone screw, said tool for securing said positioning device to said bone of the patient comprises a screwdriver, and said stop of said tool for securing said positioning device is provided by a section of a shank of said screwdriver which is larger in diameter than said at least one cylindrical opening of said template.

8. A device for attaching a positioning device to a bone of a patient at a predetermined position relative to a hip implant comprising:
    a trial hip implant with a support surface for resting on said bone of the patient;

a template that can be secured to said trial hip implant and has at least one cylindrical opening with a longitudinal axis;

wherein said trial hip implant is shaped such that any straight line which runs through one of said at least one cylindrical opening and is parallel to said longitudinal axis of a respective said at least one cylindrical opening does not intersect said trial hip implant when said template is secured to said trial hip implant; and wherein said template on a side facing away from said trial hip implant when said template is secured to said trial hip implant has a stepped surface with several steps, wherein one of said several cylindrical openings extends through each of said steps.

9. The device according to claim 8, wherein at least a portion of each of said steps has a surface which is perpendicular to said longitudinal axis of said several cylindrical opening extending through said respective step.

10. The device for treating a bone of a patient when implanting a hip implant, comprising:
a device for attaching a positioning device to a bone of a patient according to claim 5; and
at least one bone milling device comprising a receiving section for said guide section of said positioning device, wherein said guide section can be inserted into said receiving section, and said receiving section is formed such that an axis of rotation of said bone milling device is aligned along said longitudinal axis of said guide section, and said bone milling device is rotatable about said longitudinal axis of said guide section and is moveable along said longitudinal axis of said guide section when said guide section is inserted into said receiving section of said bone milling device.

11. The device according to claim 10, where said receiving section of said bone milling device comprises a stop for said distal end of said positioning device.

12. A hip implant system with:
a device for treating a bone of a patient according to claim 10;
a hip implant for receiving an artificial joint socket and comprising a support surface for resting on said bone of the patient which has a shape corresponding to the shape of said support surface of said trial hip implant; and
at least one augment that can be secured to said hip implant, wherein said augment on a side facing away from said hip implant when said augment is secured to said hip implant comprises a surface having a shape corresponding to a shape of a treatment section of one of said at least one a bone milling device.

13. A hip implant system according to claim 12, wherein said template comprises a plurality of cylindrical openings, said hip implant system comprises a plurality of augments of different sizes, and each of said at least one bone milling device comprises a treatment section having a generally spherical shape;
where each said plurality of augments is associated with one of said cylindrical openings of said template and one of said at least one bone milling device; and
where each one of said plurality of augments on the side facing away from said hip implant when said one of said plurality of augments is secured to said hip implant has a generally spherical surface, wherein a radius of said generally spherical surface corresponds to a radius of said generally spherical treatment section of said one of said at least one bone milling device which is associated with said one of said plurality of augments.

14. A system of devices for fitting a hip implant comprising:
a trial hip implant having a support surface and a spherical dome shell adapted to rest on a bone of a patient, said trial hip implant having bores positioned for attaching said trial hip implant to the bone of the patient, and plates extending radially beyond the support surface away from the spherical dome shell and separated by a notch extending between the plates through the support surface and into a curved portion of the spherical dome shell, and a threaded opening;
a template having a plurality of steps, with each of the steps having a cylindrical opening therein with a longitudinal axis, said template having a shape to fit onto said trial hip implant and an opening positioned adjacent the threaded opening, wherein the longitudinal axis of each of the cylindrical openings in the steps align with the notch and one of the cylindrical openings is positioned radially on either side of the support surface when said template is fitted onto said trial hip implant;
a fastener, said fastener placed through the opening in said template and threaded into the threaded opening of said trial hip implant, whereby said trial hip implant and said template are capable of being removable attached together;
a bone drill sized to fit though the cylindrical openings, whereby the cylindrical openings in said template guides said bone drill in drilling the bone of the patient in a predetermined direction;
a positioning device having threads and a diameter adapted to pass through the cylindrical openings and into the bone of the patient;
a tool removably attaching to said positioning device, whereby said positioning device is capable of being rotated by said tool, said tool has a portion passing through the cylindrical openings and having a tool stop positioned to contact one of the plurality of steps preventing the tool stop from passing through the cylindrical openings, whereby said positioning device is positioned at a predetermined depth; and
a bone milling device having strut members and a receiving section adapted to receive said positioning device, the receiving section having a receiving section stop, whereby after removal of said trial hip implant and said template said bone milling device is capable of removing the bone of the patient until a distal end of said positioning device contacts the receiving section stop,
whereby upon removing said positioning device a final hip implant is capable of being attached to the bone of the patient.

15. A device for attaching a positioning device for locating a bone milling device used in placement of an augment for a final hip implant comprising:
a trial hip implant having a support surface and a spherical dome shell configured to fit within a hip bone, the trial hip implant having plates extending radially beyond the support surface away from the spherical dome shell and separated by a notch, the notch extending between the plates through the support surface and into a curved portion of the spherical dome shell; and
a template having a plurality of openings attached to the trial hip implant over the support surface and a portion of the spherical dome shell, wherein the plurality of openings align with the notch and one of the plurality of openings is positioned radially on either side of the support surface, whereby said template and the plurality of openings are capable of guiding a drill for forming a hole in the hip bone for placement of the positioning device used to locate a bone milling device for removing hip bone to a predetermined depth before attachment of the finial hip implant and augment to the hip bone.

16. A method of placing a positioning device for locating a bone milling device and placement of a final hip implant and an augment for a hip implant comprising the steps of:

attaching a trial hip implant to a hip bone, the trial hip implant having a support surface and a spherical dome shell configured to fit within the hip bone, the trial hip implant having plates extending radially beyond the support surface away from the spherical dome shell and separated by a notch, the notch extending between the plates through the support surface and into a curved portion of the spherical dome shell;

attaching a template having a plurality of openings to the trial hip implant over the support surface and a portion of the spherical dome shell, wherein the plurality of openings align with the notch and one of the plurality of openings is positioned radially on either side of the support surface;

inserting a drill through a selected one of the plurality of openings and through the notch in the trial hip implant;

drilling a hole in the hip bone with the drill;

inserting a positioning device through the selected one of the plurality of openings, through the notch, and into the hole;

removing the trial hip implant from the hip bone;

using the positioning device to locate a bone milling device and removing hip bone to a predetermined depth; and removing the positioning device from the hip bone, whereby the final hip implant and the augment are capable of being secured to the hip bone.

* * * * *